United States Patent
Holland et al.

(10) Patent No.: US 6,817,978 B2
(45) Date of Patent: Nov. 16, 2004

(54) ILLUMINATED RETRACTOR FOR USE IN CONNECTION WITH HARVESTING A BLOOD VESSEL FROM THE ARM

(75) Inventors: Donna D. Holland, Roswell, GA (US); John D. Pond, Jr., Lilburn, GA (US); Douglas G. Evans, Snellville, GA (US)

(73) Assignee: Teleflex-CT Devices Incorporated, Limerick, PA (US)

( * ) Notice: Subject to any disclaimer, the term of this patent is extended or adjusted under 35 U.S.C. 154(b) by 0 days.

(21) Appl. No.: 10/055,778

(22) Filed: Jan. 23, 2002

(65) Prior Publication Data

US 2003/0139651 A1 Jul. 24, 2003

(51) Int. Cl.$^7$ .................................................. A61B 1/32

(52) U.S. Cl. ...................... 600/212; 600/210; 600/213; 600/215; 600/235; 600/245

(58) Field of Search .................................. 600/212, 215, 600/210, 235, 245, 213, 185, 191, 193, 190, 196, 201, 226; 606/190

(56) References Cited

U.S. PATENT DOCUMENTS

| | | |
|---|---|---|
| 2,646,037 A | 7/1953 | Cook et al. |
| 3,638,644 A | 2/1972 | Reick |
| 4,052,980 A | 10/1977 | Grams et al. |
| 4,597,030 A | 6/1986 | Brody et al. |
| 4,765,701 A | 8/1988 | Cheslak |
| 4,836,190 A | 6/1989 | Zwick |
| 4,934,352 A | 6/1990 | Sullivan, Jr. |
| 4,996,976 A | 3/1991 | Nakagawa |
| 5,005,108 A | 4/1991 | Pristash et al. |
| 5,035,232 A | 7/1991 | Lutze et al. |
| 5,514,076 A | 5/1996 | Ley |
| 5,514,077 A | 5/1996 | Rabban |
| 5,667,480 A | 9/1997 | Knight et al. |
| 5,722,934 A | 3/1998 | Knight et al. |
| 5,725,479 A | 3/1998 | Knight et al. |
| 5,730,748 A | 3/1998 | Fogarty et al. |
| 5,776,159 A | 7/1998 | Young |

(List continued on next page.)

FOREIGN PATENT DOCUMENTS

| | | |
|---|---|---|
| GB | 2133694 | 8/1984 |
| WO | WO 97/13462 | 4/1997 |
| WO | WO 99/01696 | 1/1999 |
| WO | WO 99/56633 | 11/1999 |
| WO | WO 01/00093 | 1/2001 |

OTHER PUBLICATIONS

Auto Suture Company, The Mini–Harvest System (1996).

Design News, Bypass Surgery Made Easier, Disposable Instruments, Made from Standard Plastics, Key to Minimally Invasive Procedure for Extracting Veins, Gary Chamberlain, Senior Editor, pp. 57–58, 60, 62 (Jan. 6, 1997).

(List continued on next page.)

*Primary Examiner*—Cary E. O'Connor
(74) *Attorney, Agent, or Firm*—Dechert, LLP; John W. Ryan

(57) ABSTRACT

An illuminated surgical retractor for defining and illuminating a subcutaneous surgical field in the space near a vessel (such as the radial artery or the basilic vein) during a procedure for harvesting the vessel, wherein the illuminated surgical retractor includes a handle member pivotally connected at an acute angle to a first elongate section that has a non-liner shape, and includes a second elongate section releasably connected to the first elongate section, wherein a portion of the second elongate section defines an illumination input end portion, which is optically coupled to a light source to substantially illuminate the second elongate section, and further including an insertion area positioned on the proximal end portion of the first elongate section to allow the second elongate section to be inserted into the first elongate section.

45 Claims, 8 Drawing Sheets

U.S. PATENT DOCUMENTS

| | | | |
|---|---|---|---|
| 5,797,947 | A | 8/1998 | Mollenauer |
| 5,853,417 | A | 12/1998 | Fogarty et al. |
| 5,904,650 | A | 5/1999 | Wells |
| 5,921,919 | A | 7/1999 | Chin et al. |
| 5,967,971 | A | 10/1999 | Bolser |
| 5,972,010 | A | 10/1999 | Taheri |
| 6,007,487 | A | 12/1999 | Foley et al. |
| 6,033,361 | A | 3/2000 | Co et al. |
| 6,042,538 | A | 3/2000 | Puskas |
| 6,193,651 | B1 | 2/2001 | DeFonzo |
| 6,196,968 | B1 | 3/2001 | Rydin et al. |
| 6,228,025 | B1 * | 5/2001 | Hipps et al. ............... 600/213 |
| 6,322,499 | B1 * | 11/2001 | Evans et al. ............... 600/212 |
| 6,554,768 | B1 * | 4/2003 | Leonard .................... 600/213 |

OTHER PUBLICATIONS

Dimitri, W. R. et al., A Quick and Atraumatic Method of Autologous Vein Harvesting Using the Subcutaneous Extraluminal Dissector, J. Cardiovasc. Surg., vol. 28, pp. 103–111 (1987).

Dregelid, E. et al., Endothelial Cell Injury in Human Saphenous Veins After Manipulation and Tweezer Grasping, J. Cardiovasc. Surg., vol. 29, pp. 464–469 (1988).

Gundry, Steven R. et al., Optimal Preparation Techniques for Human Saphenous Vein Grafts, Surgery, No. 6, pp. 785–794 (Dec. 1980).

Hauer, G. et al., Endoscopic Subfascial Discission of Perforating Veins, Surg. Endosc., vol. 2, pp. 5–12 (1988).

Meldrum–Hanna, W. et al., Long Saphenous Vein Harvesting, Aust. N.Z. J. Surg., vol. 56, pp. 923–924 (1986).

Moazami, Nader et al., Minimally Invasive Greater Saphenous Vein Harvesting for Coronary Artery Bypass Surgery, Surgical Rounds, pp. 94–97 (Mar. 1997).

Rashid, A. et al., Subcutaneous Technique for Saphenous Vein Harvest, The Annals of Thoracic Surgery, vol. 37, No. 2, pp. 169–170 (Feb. 1984).

Snowden Pencer DSP, The Diamond–Line of Surgical Instruments Brochure, Tebbetts EndoPlastic Instrument System, 1995.

Snowden Pencer DSP, EndoCABG System, Innovative Instrumentation for Endoscopic Coronary Artery Bypass Grafting, 1996.

Lee, John, Surgical Physician Assistant, Minimally Invasive Vein Harvesting, pp. 26–32, Nov./Dec. 1996.

Wheatley, D. J., Autocoronary bypass Grafting Techniques, Surgery of Coronary Artery Disease, pp. 348–349 (Date Unknown).

* cited by examiner

ILLUMINATED RETRACTOR FOR USE IN CONNECTION WITH HARVESTING A BLOOD VESSEL FROM THE ARM

BACKGROUND OF THE INVENTION

1. Field of the Invention

The present invention relates to medical devices, and, in particular, to a retractor for harvesting a blood vessel, which, in turn, is used in connection with an ongoing or subsequent surgical procedure. More particularly, the present invention provides such a retractor that is capable of defining and illuminating a subcutaneous working space to ameliorate accessibility to, and to facilitate visualization and harvesting of one or more blood vessels (e.g., radial artery, basilic vein) for grafting/transplantation in connection with a surgical procedure (e.g., coronary bypass surgery).

2. Description of Related Art

In certain surgical procedures, it is necessary to remove a portion (or even the entirety) of a patient's blood vessel for use in another, often remotely located part of that, or a different patient's body. For example, it is known to remove/excise some or all of a patient's radial artery, saphenous vein, cephalic vein, basilic vein or mammary artery for transplantation in connection with a coronary bypass surgical procedure. Once transplanted, the removed section (or entirety) of the vein/artery functions as a graft that replaces both the coronary arteries, which, as a result of aging and/or disease, have become blocked by plaque deposits, stenosis, or cholesterol, thus severely inhibiting their ability to supply life-sustaining blood to the patient's heart.

In some instances, these blockages can be treated with angioplasty, atherectomy or stent placement, and, therefore, coronary bypass surgery is not warranted. Quite often, however, a coronary bypass is required because these treatment methods are either contraindicated, or have proven incapable of removing blockages from coronary arteries.

According to current coronary bypass surgery techniques, a blood vessel is harvested from elsewhere within a patient's body and grafted into a locus between the patient's aorta and the coronary artery beyond the point of blockage. It is preferred to use a blood vessel taken from the patient undergoing bypass surgery, since he/she is a ready source of suitable vessels that will not be rejected by his/her own body after transplantation.

It has been found that each of a patient's radial or mammary artery, or saphenous, cephalic or basilic vein has functional and structural characteristics (e.g., diameter) resembling those of the coronary arteries, thus rendering any of these vessels potential candidates for grafting.

Among these vessels, however, the radial artery and the saphenous vein are often favored for transplantation in connection with coronary bypass surgery, likely due to the comparative ease of their harvesting and/or the comparative lack of complications (especially post-operative) associated with their harvesting and/or their subsequent transplantation.

Harvesting the saphenous vein entails making an incision in a patient's leg, and then pulling away layers of fatty tissue to reveal the saphenous vein, which is then carefully removed.

Until recently, the incision that was made to access the saphenous vein was quite long—spanning a patient's groin to at least his/her knee, and often to his/her ankle. Making this "fillet-like" incision inherently presents a serious risk of injury to the medial lymph bundle and/or to nerves located within the leg, as well as a realistic risk of infection to the incision site.

Moreover, the healing process associated with this long, "fillet-like" incision is protracted (often more prolonged than the incision(s) to the patient's chest in furtherance of the coronary bypass) and very painful, especially if the patient has circulation problems in his/her extremities. Ultimately, in fact, the incision often does not heal properly, thus requiring medical attention and/or invasive procedures (e.g., corrective surgery).

As indicated in U.S. Pat. No. 6,193,651 to DeFonzo, U.S. Pat. No. 6,228,025 to Hipps et al, and U.S. Pat. No. 6,322,499 to Evans et al., however, techniques now exist that allow the saphenous vein to be harvested by making several (usually either 2 or 3) smaller incisions on the proximal thigh, at the level of the knee joint, and, optionally, the inner malleolus.

In accordance with these techniques, a retractor is inserted into each of these incisions to define, access and illuminate the subcutaneous space. The retractor is used to form a skin bridge to allow for retraction of the fatty tissue surrounding the saphenous vein, which is then harvested.

Unfortunately, despite this advancement, many patients are not ideal candidates for saphenous vein harvesting by virtue of having an unacceptably high risk of minor to extensive complications associated with even these smaller leg incisions. Such patients include the elderly, the obese, diabetics, those who have developed extensive varicose veins in their legs, those who have fragile veins in their legs due to taking or having previously taken certain medications, and those whose saphenous vein is in a position that does not readily lend itself to harvesting.

These same patients, however, often are ideal candidates for other vessel harvesting options, such as radial artery harvesting, in which the radial artery is harvested from a patient's arm (usually his/her non-dominant arm). The radial artery is one of two arteries—the ulnar artery is the other—in a patient's forearm. Both these arteries stem from the brachial artery (the radial artery being the true continuation of the brachial artery) and, together, form a network of vessels, which supply blood to the wrist and hands, and which rejoin to form the palmar arch at the palm of the hand.

Radial artery harvesting is contraindicated in only a few classes of patients, such as those who have carpal tunnel syndrome, Raynaud's syndrome, and those who have severe kidney disease or poor blood circulation to their fingers.

Harvesting the radial artery for transplantation/grafting in connection with coronary bypass surgery historically involved making a continuous, "fillet-like" incision from approximately two inches below (i.e., toward the hand) the patient's elbow at the antecubital fossa to about one inch above (i.e., toward the elbow) the patient's wrist. The length of such an incision was reported, on average, to be about 23 cm (i.e., about 9 inches). A. Uchida et al., *Endoscopic Harvesting of Radial Artery Graft for Coronary Artery Bypass*, Ann. Plast. Surg. 1998;41:459–463).

Just as making a "fillet-like" incision causes significant risks in the context of saphenous vein harvesting, making an approximately 23 cm (i.e., 9 inch) continuous cut into a patient's arm to harvest the radial artery also presents serious risks, such as severing the delicate superficial radiac and/or lateral antebrachial cutaneous nerves.

In an effort to avoid these risks, it has been proposed (and is currently practiced) to instead make two, transverse, 2–3 cm in length incisions—one at the patient's wrist, and the another 4 cm from the patient's antecubital fossa (see, e.g., Y. Terada et al., *Endoscopic Harvesting of the Radial Artery as a Coronary Artery Bypass*, Ann. Thorac. Surg.

1998;66:2123–4, and A. Uchida et al., *Endoscopic Harvesting of Radial Artery Graft for Coronary Artery Bypass*, Ann. Plast. Surg. 1998;41:459–463). Alternate loci for these two, tranverse incisions have also been proposed/practiced, including at 4 cm from the patient's wrist, and at the middle region of the patient's forearm (see Z. Galajda et al., *Minimally Invasive Harvesting of the Radial Artery as a Coronary Atery Bypass Graft*, Ann. Thorac. Surg. 2001;72:291–3).

Although specific radial artery harvesting techniques may differ with respect to equipment used and/or approach taken, they generally entail (once the two transverse cuts are made) inserting a retractor within each of these incisions to lift the skin and tissue (i.e., the deep fascia) located directly beneath the skin, thus forming several skin bridges between the incisions, and defining subcutaneous space beneath the skin bridges.

Generally, any remaining deep fascia tissue is then transected to reveal the bracioradialis and flexor carpi muscles, which are pushed aside to expose the neurovascular fascia, which are transected to reveal the radial artery within loose areolar tissue. The areolar tissue is then displaced to allow the radial artery to be harvested (e.g., by hand, with one or more tools)

Regardless of the size and placement of the incisions that are made within the patient's arm, most radial artery harvesting techniques (including the Terada and Uchida techniques) necessarily rely upon the use of several instruments. Among these, generally, is an endoscopic apparatus, which provides visualization of the subcutaneous surgical field and, optionally, provides a lumen, through which tools may be introduced during the harvesting procedure, and/or through which the excised radial artery (or other tissue) may be withdrawn.

There are several notable drawbacks associated with using endoscopic technology for visualization of the subcutaneous space in connection with radial artery harvesting. First, the endoscope (or the display unit that depicts its image) provides a distorted visual perspective, which is a poor substitute for actual visualization of the surgical field by the naked eye. Second, compounding the first drawback, use of an endoscope provides for visualization of only a small portion of the subcutaneous space, namely, the area that is immediately in front of the endoscope. Third, illumination within the subcutaneous space created by this type of endoscope is also limited to the light emitted directly at the distal portion of the endoscope.

Because of these disadvantages, there is a significant learning curve to safely and efficiently practice this radial artery harvesting procedure.

Other drawbacks also are caused when attempting to use conventional equipment in connection with the skin bridging radial artery harvesting procedure. For example, because the skin bridges between the transverse incisions are quite long, it is difficult to sufficiently illuminate the subcutaneous space, especially when conventional, non-illuminated retractors are implemented/utilized.

Moreover, the area from which certain vessels are harvested may have smaller, narrower dimensions than the most other bodily areas within which vessels to be harvested are located. For example, a patient's arm (in which both the radial artery and the basilic vein are located) is comparatively narrower than his/her leg, in which the saphenous vein is located. As such, the subcutaneous space within a patient's arm is likely comparatively more crowded with instruments during the harvesting process, thus complicating the process and further prolonging the learning curve for safely and efficiently practicing radial artery harvesting.

Therefore, a need exists for a procedure that overcomes the aforementioned visualization- and illumination-related drawbacks, as well as the spatial limitations that individually and collectively plague conventional radial artery harvesting techniques and prolong the learning curve required for medical personnel to safely, yet expeditiously practice such techniques.

SUMMARY OF THE INVENTION

The present invention provides a surgical retractor that meets this, and other needs. As shown in the drawings, the present invention provides a retractor for defining, accessing and illuminating a subcutaneous working space near a blood vessel (e.g., the radial artery, the basilic vein) located within a patient's arm in order to facilitate safe, reliable and expeditious harvesting of the vessel.

In an exemplary procedure for harvesting a patient's radial artery, two small transverse (i.e., 2–3 cm) incisions are made in a patient's non-dominant arm. The incisions are made either at the patient's wrist and 4 cm from the patient's antecubital fossa, or at 4 cm from the patient's wrist and at the middle region of the patient's forearm.

The surgical retractor of the present invention is inserted underneath the skin at one of the incision sites, and is used to lift a skin bridge and, preferably, some layers of the deep fascia as well. This lifting action defines a subcutaneous space, which is illuminated by the retractor to allow for visualization of the tissue and muscle located therein.

The retractor is retained in place via, for example, an external retention device attached to both the retractor and to a structure (e.g., the table on which the patient lies), thus allowing for the defined subcutaneous space to be maintained and illuminated. This, in turn, allows medical personnel use of its/their hands to locate and dissect any remaining deep fascia, thus exposing muscle (e.g., the bracioradialis and flexor carpi).

The muscle is moved (e.g., by hand or, preferably, with an instrument) to reveal neurovascular fascia, which is dissected to reveal the radial artery within loose areolar tissue. This tissue is then displaced (e.g., with an instrument or, preferably, by hand) to reveal the radial artery, which is then harvested according to techniques known to the ordinarily skilled artisan.

The illuminated retractor of the present invention provides a large, well-illuminated surgical field, which preferably extends the substantial length of the retractor within the subcutaneous space created by the retractor, and which, consequently, allows for illumination and improved visualization of the tissue and muscle that is located within the subcutaneous space, and that surrounds the radial artery. This, in turn, facilitates the harvesting procedure, and limits the risk of harming the delicate superficial radiac and/or lateral antebrachial cutaneous nerves.

The illuminated surgical retractor preferably has a handle member, a first elongate section and a second elongate section. The handle member is contoured to be gripped by medical personnel, and, in a preferred aspect of the invention, is pivotally connected to the first elongate section at the distal end portion of the first elongate section to permit one-handed use of the retractor by medical personnel.

Unless indicated otherwise, the term "medical personnel," as used herein, is intended to refer to a single individual that has a role in connection with a surgical procedure. The specific medical personnel who performs a given task in connection with the procedure described herewithin is determined based on the particular task, the level of training required to perform the task, and the availability of other medical personnel.

The handle member permits the retractor to be lifted at any desired angle with respect to the axis of the vessel (e.g., the radial artery). Application of a pulling force to the handle member results in a corresponding pulling or retraction force being applied to the skin and/or subcutaneous tissue via the first elongate section.

In an exemplary aspect of the invention, an elongated rod portion extends from the handle member. The rod portion allows the retractor to be maneuvered into a desired position by medical personnel and then fixed in this position by clamping or grasping the retractor with the available operating table retention mechanism(s).

The first elongate section of the retractor, which is preferably made of a metal or alloy, has a first elongate proximal end portion, a first elongate distal end portion, a first elongate outer surface, and a first elongate inner surface, and functions to transfer lifting and/or insertion forces from the handle member to the skin bridge of the patient.

In an exemplary aspect of the present invention, at least a portion of the first elongate section preferably is non-linear. Preferably, this non-linear area is either curved or bent, and spans at least the area between the first elongate proximal end portion and the first elongate distal end portion.

The second elongate section, which is preferably made of a semi-rigid material that is substantially transparent, has a second elongate proximal end portion, a second elongate distal end portion, a second elongate outer surface and a second elongate inner surface, and functions to perform the illumination feature of the present invention.

The second elongate section is either substantially straight (e.g., when the first elongate section is curved) or bent (e.g., when the first elongate section is bent), and is preferably slidable laterally with respect to a portion of the first elongate section and into engagement with the first elongate section such that the first and second elongate sections are substantially adjacent to each other while engaged.

As used herein, reference to the proximal end portion of an element is intended to denote the end portion of an element that is spaced apart from the handle member, and reference to the distal end portion of an element is intended to denote the end portion of an element that is generally adjacent to or closer to the handle member of the present invention.

The first elongate proximal end portion of the first elongate section preferably has a rounded shape or a smoothly radiused pointed shape that allows the retractor to be pushed into any of the transverse incisions. Once so inserted, the retractor can be safely pushed forward underneath the skin, and into/within the deep fascia.

Additionally, the first elongate proximal end portion of the first elongate section preferably includes an insertion area to receive and retain the proximal end portion of the second elongate section, and to ensure that these portions remain adjacent to each other during the harvesting procedure. In a preferred aspect of the invention, the insertion area is a substantially U-shaped flap or loop into which the proximal end portion of the second elongate section is laterally, securely insertable.

Although the insertion area should protrude from the first elongate section enough to allow for insertion of the second elongate section therein, it also should provide a low profile extension that does not deter dissection of the tissue, and that ensures that the inserted second elongate section will not become dislodged therefrom during the harvesting procedure.

The proximal end portion of the second elongate section preferably has a rounded shape or, alternatively, a smoothly radiused pointed shape. The shape of the second elongate section proximal end portion is selected to allow for insertion thereof into the insertion area of the first elongate section. Its shape also should ensure that the proximal end portion of the retractor, when the first and second elongate sections are connected, can readily penetrate tissue as the retractor is inserted into a small incision and maneuvered into position, and that the proximal end portion of the second elongate section will be securely retained in the insertion area.

Moreover, the proximal end portion of the second elongate section also is preferably configured/shaped to direct light forwardly of the retractor (in addition to the light that emanates from, and extends the substantial length of the retractor) during use to allow for improved visualization of the subcutaneous space in connection with the harvesting procedure.

The retractor of the present invention also preferably includes a bent dissecting tip, which extends from the first elongate section at the proximal end portion of the first elongate section. This tip allows medical personnel to use the retractor as a dissecting device while the retractor is being maneuvered into, around and/or through the connective tissue and muscle surrounding the radial artery. The tip may include serrations thereupon to assist in the dissection of the tissue, and in retaining the retractor in its desired position during the harvesting procedure.

In order to enhance the reflective qualities of the illuminated retractor, the first elongate inner surface of the first elongate section may include a mirrored surface thereon. Also, the second elongate inner surface of the second elongate section may have a machined or molded (e.g., injection molded) micro-lens surface thereon that refracts light forwardly at a desired angle.

In an alternate aspect of the invention, the second elongate section may have a graded dot screen surface. The mirrored surface of the first elongate inner surface, and the machined surface of the second elongate inner surface function to minimize the light intensity loss of the light energy that is provided to the surgical field by the illuminated retractor.

In yet another alternate aspect of the invention, the second elongate inner surface may be reflective, in order to direct illumination outwardly from the second elongate outer surface. Furthermore, the second elongate section may be constructed so as to reflect to the illumination forwardly from the second elongate section to illuminate the skin bridge forwardly of the illuminated surgical retractor.

For example, the second elongate section may be formed so that the light is transmitted at a forward angle that is preferably between about 15° and 75°, and, more preferably, between about 30° and 60° relative to the second elongate section, and so that illumination may be scattered to the sides of the retractor as desired.

A preferred form of the retractor also includes a connector, preferably a twist type connector, between the handle member and the first and second elongate sections. This allows for a simple connection (e.g., a one-quarter turn) to reversibly but assuredly secure the first elongate section to the handle with confidence that these components will remain attached as the skin bridge is defined/created and maintained.

The connector also connects the handle member to the second elongate section to ensure that the light energy travels from the light source, through the handle member, and into the second elongate section. The light energy fills the second elongate section such that light energy is radiated from the second elongate section into the subcutaneous space defined by the retractor.

In this manner, light can be provided from the light source via the optical cable to the illumination input end portion of the second elongate section so that the second elongate section is illuminated, thus resulting in an illuminated surgical field.

A further feature of a preferred form of the present invention is that the distal end portion (or heel portion) of the illuminated retractor is formed to shield all nearby medical personnel from the light created by the distal end portion of the second elongate section. Additionally, the first elongate section may include a side channel in a shaft portion thereof to allow a shaft shaped portion of the second elongate section to be inserted therethrough, thus allowing the second elongate section to be replaceably mounted onto the first elongate section as desired.

A further feature of the illuminated retractor of the present invention is that at least a portion of the shaft shaped portion and/or the distal end portion of the second elongate section is preferably spaced apart from at least a portion of the shaft portion and/or the distal end portion of the first elongate section to ensure that there is no heat buildup between these elements of the retractor.

Still other features of a preferred form of the retractor of the present invention are that the light cable passes through the handle member of the retractor, and that a portion of the handle member may be formed to allow the light generated by the light cable to be observed through the body of the handle member. These features enable medical personnel using the retractor to readily determine whether or not the light source for the retractor is in operation.

Additionally, in a further preferred aspect of the invention, the retractor may include a second connection that may be used to connect a standard light cable at the top of the handle member to a shortened light cable in the handle member of the retractor, so that the handle member and elongate members may be packaged and/or sterilized separately. Alternately, the light cable may be allowed to pass through the handle member for direct connection to the light source and the second elongate member as desired.

Still other aspects, embodiments and advantages of the present invention are discussed in detail below.

BRIEF DESCRIPTION OF THE DRAWINGS

For a fuller understanding of the nature and desired objects of the present invention, reference is made to the following detailed description taken in conjunction with the accompanying figures, wherein like reference characters denote corresponding parts throughout the views, and in which.

DETAILED DESCRIPTION OF THE INVENTION

Figure 1:
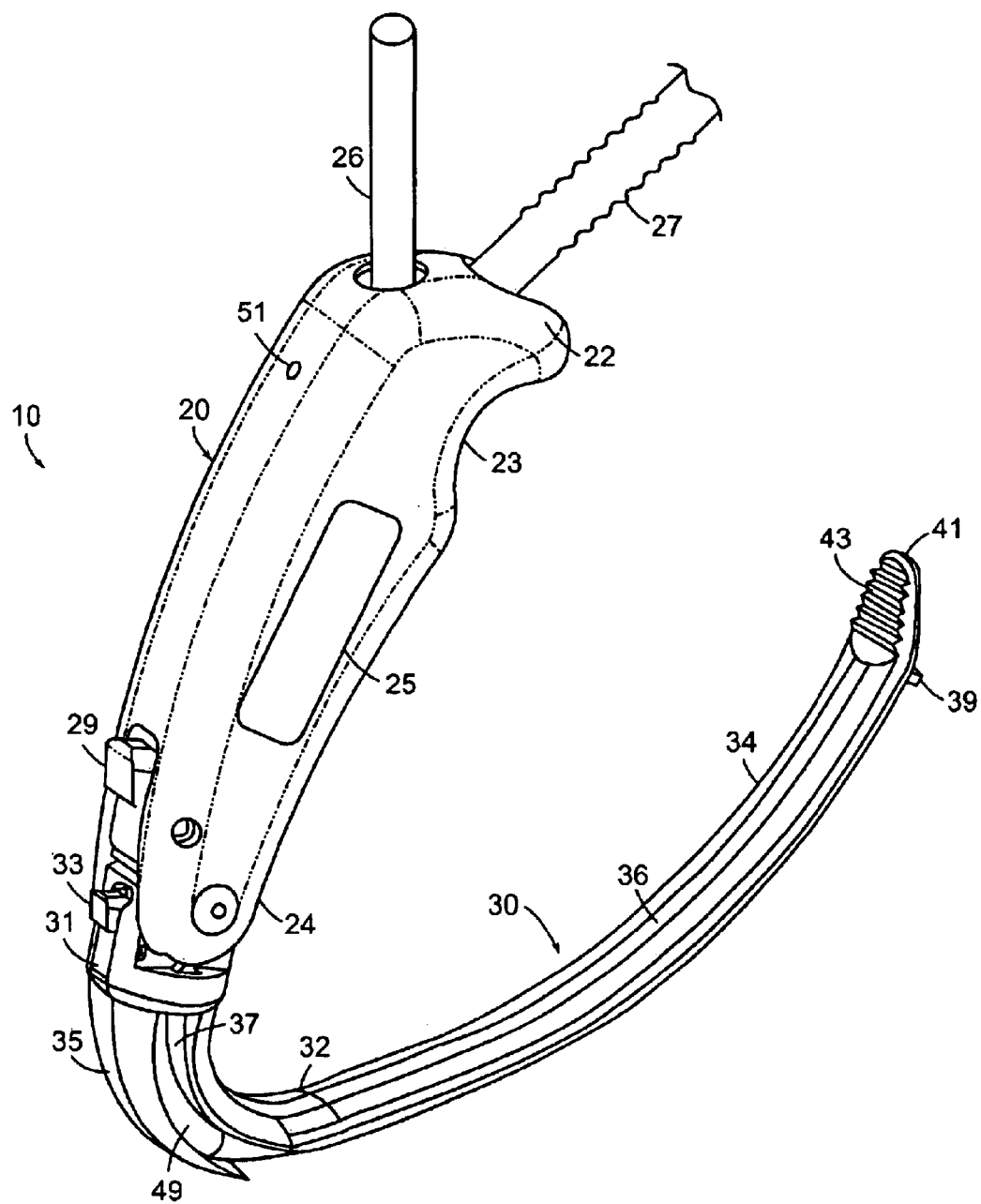
FIG. 1 is a perspective view of a preferred form of an illuminated retractor according to the present invention.

The present invention provides an illuminated retractor for assisting in accessing, defining and illuminating the subcutaneous space within a patient's arm in which a blood vessel (e.g., the radial artery, the basilic vein) is located, thus allowing for improved visualization of this space, and, in turn, facilitating a procedure wherein the vessel is harvested.

As shown in the drawings, the present invention provides an illuminated surgical retractor 10 having a handle member 20, a first elongate section 30, a second elongate section 40, and a twist connector 31.

The handle member 20 is an elongate and generally cylindrical member that has a first top handle member end portion 22 and a second bottom handle member end portion 24. The second handle member end portion 24 of the handle member 20 is connected to the first elongate section 30 of the retractor 10 at the shaft portion 35 distal to the distal end portion 32 of the first elongate section 30. This connection is made via a twist connector 31 to permit one-handed setup and use by medical personnel.

Figure 2:
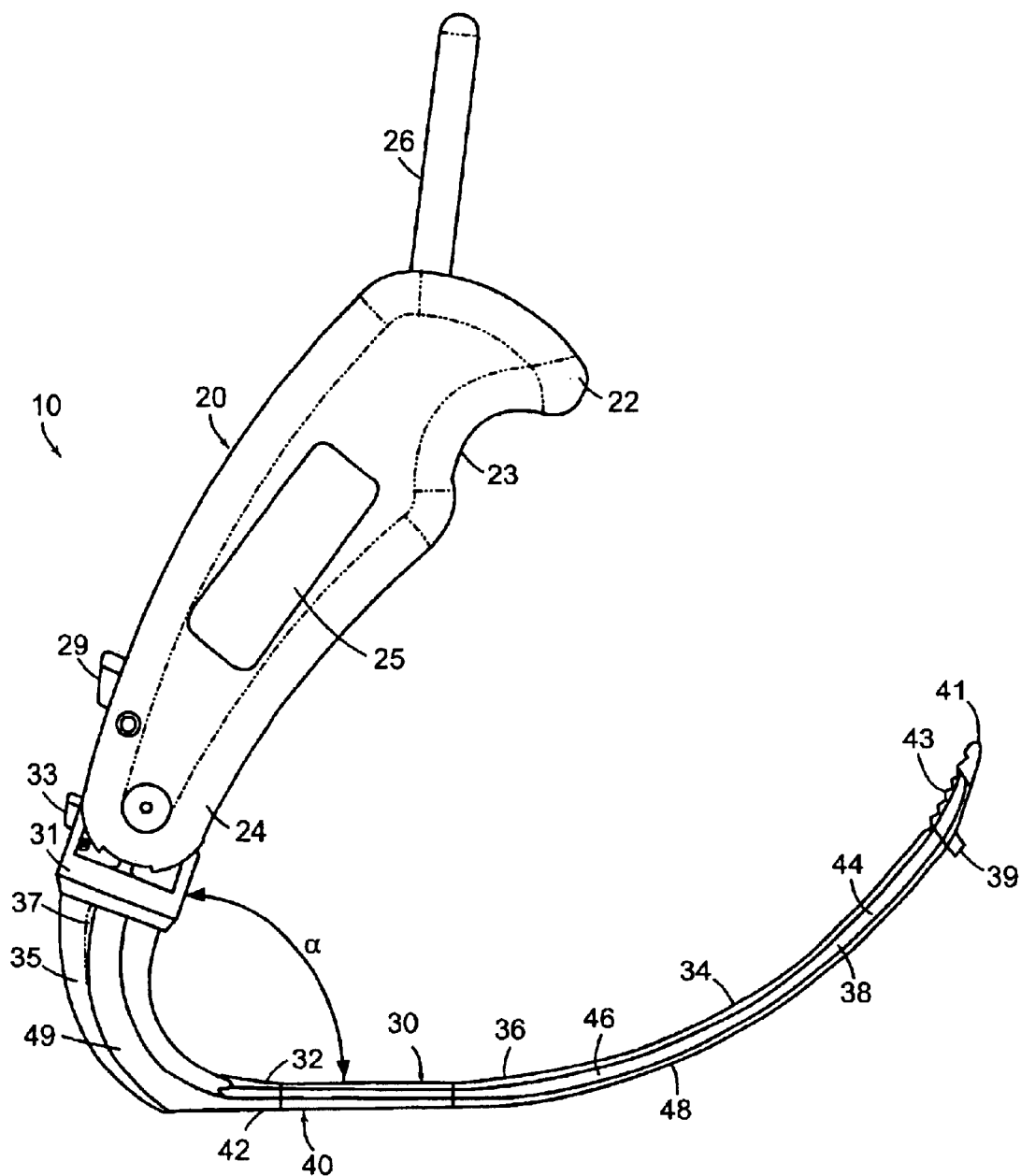
FIG. 2 is an enlarged side view of the retractor of FIG. 1 with the optical cable removed for clarity.
Figure 3:
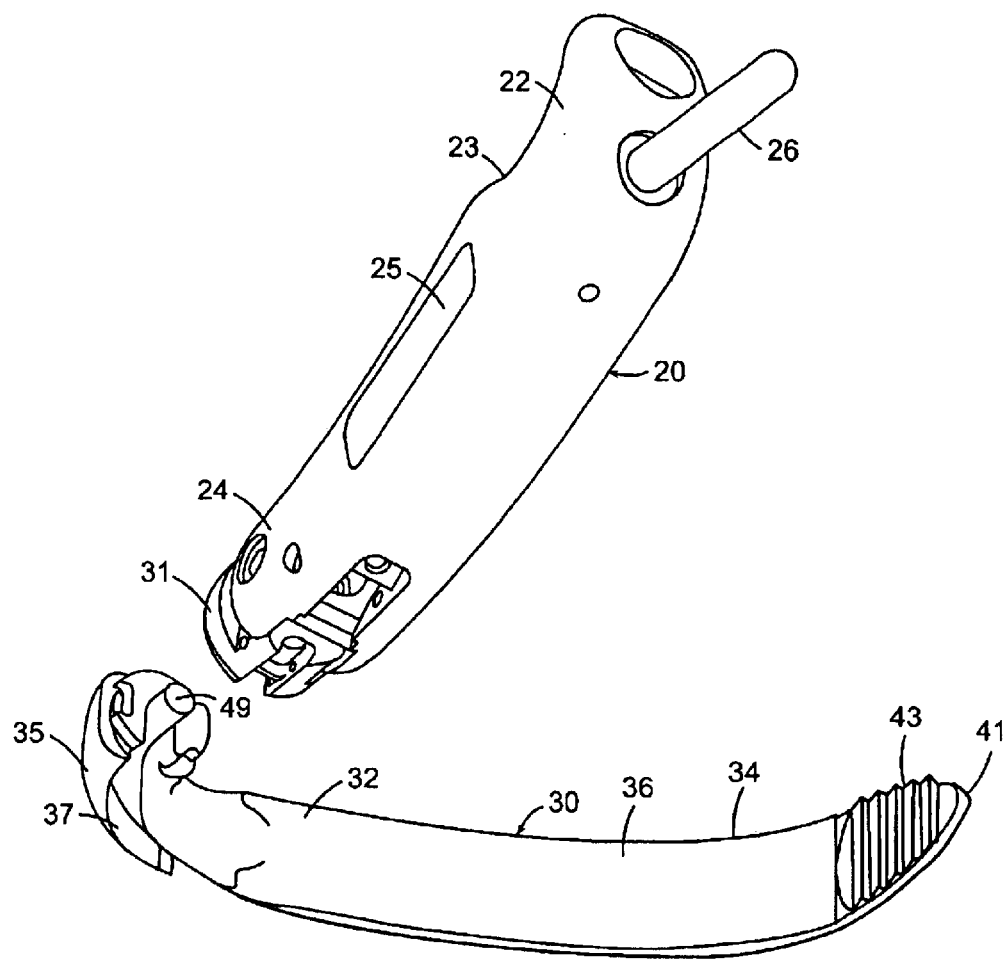
FIG. 3 is an exploded perspective view of an illuminated retractor according to the present invention showing the handle member separated from the first elongate section and the second elongate section, and with the optical cable removed for clarity.

The best combination of retractor mobility and application of retractive or pulling force occurs when an acute angle, $\alpha$, is defined between the handle member 20 and the first elongate section 30. Preferably, this angle, $\alpha$ (see FIG. 2), is between about 30° and 90°, more preferably between about 45° and 75°.

The handle member 20 permits the retractor 10 to be lifted at nearly any angle with respect to the axis of the blood vessel to be harvested. Therefore, when an upward or pulling force is applied to the handle member 20, a retractive force is applied to the subcutaneous tissue (or other body matter) via the first elongate section 30. Such action is effective to create/define a subcutaneous space beneath, and skin bridge above the subcutaneous tissue by virtue of the subcutaneous tissue and overlying skin being drawn upwardly by the first elongate outer surface 36 of the first elongate section 30 of the retractor 10.

In the context of a radial artery harvesting procedure, application of this force causes separation of at least a portion of the deep fascia that lies under the skin, and also causes formation of a skin bridge between incision sites. This allows medical personnel access to underlying tissue and muscle, which, once dissected or moved, reveals the radial artery.

The handle member 20 of the retractor 10 also preferably includes a finger grip surface 23 that is preferably contoured to be gripped by the hand of medical personnel to provide more tactile feel and feedback, and to increase the medical personnel's comfort in using and maneuvering the retractor in connection with the harvesting procedure.

The handle member 20 also preferably includes a window area 25 to provide visual confirmation that the light source is operative, and that the retractor 10 is properly set up—that is, when the retractor 10 is illuminated, the window area 25 is illuminated so that medical personnel (and any other people in the surgical suite) will be able to readily determine that the retractor is in use. In a preferred form of the present invention, the illumination of the window area 25 is accomplished by providing a window in the handle member 20 to enable the light generated by the optical cable 27 to shine therethrough as the optical cable 27 extends through the interior of the handle member.

The handle member 20 also preferably includes a flush port 51 to assist in the cleaning and re-sterilization of the handle member.

The handle member 20 may also have an elongated rod 26 that extends upwardly from the first handle member end portion 22. The rod 26 allows the retractor 10 to be fixed or grasped by various operating table mechanisms (not shown) known in the art, so that the retractor 10 may be fixed in a desired position. These known operating table mechanisms are presently used in the art to support various types of equipment around the surgical field. They are typically attached at one end to the operating table, and include one or more manipulable joints to allow the user to adjust the orientation of a medical device relative to the patient and the operative field.

Use of the operating table mechanism and the elongated rod 26 allows the retractor 10 to be maneuvered into a desired position by medical personnel, and then fixed in that position, thus not requiring any medical personnel to maintain a hold (with either one or two hands) upon the retractor in order to retain it at this desired position.

This, in turn, uncrowds the surgical area both at and near the vessel harvesting site (e.g., a patient's arm in the case of radial artery or basilic vein harvesting), and "frees more hands" for performing a variety of tasks relating to the harvesting procedure (e.g., dissecting and/or moving tissue and muscle, excising the vessel, etc.).

The first handle member end portion 22 of the present invention also preferably includes an optical cable 27 that extends therefrom. In a preferred form of the present invention, the optical cable 27 is flexible and extends from a twist connector 31 on the proximal portion of the handle member 20 to a conventional light source (not shown).

In an alternate, yet also preferred form of the present invention, the first handle member end portion 22 includes a second connector 54 (see FIGS. 7A and 7B) thereon to allow medical personnel to connect a standard length of optical cable thereto. The optical cable 27 is then connected to a conventional light source. In an embodiment in which two connectors 31, 54 are utilized, the optical cable 27 is connected to a short cable 56 at the second connector 54, and then the second elongate section 40 is connected to the short cable 56 at the twist connector 31.

The second handle member end portion 24 is preferably pivotally connected to the first elongate section 30. As shown, the second handle member end portion 24 preferably includes a depressible pivot knob 29 thereon to actuate the hinge/pivot mechanism located in the interior of the handle member 20. Depression of the pivot knob 29 enables the user to pivot the first elongate section 30 relative to the handle member 20. When the pivot knob 29 is released, the first elongate section 30 and the handle member 20 are fixedly retained relative to each other.

In a preferred form of the present invention, this hinge/pivot mechanism provides a mechanical joint to connect the first elongate section 30 to the handle member 20. Because the optical cable 27 and/or short cable 56 are preferably flexible, and provide for the transfer of light energy therethrough, the pivoting of the handle member 20 relative to the first elongate section 30 does not affect the connection between the optical cable 27 or short cable 56 and the second elongate section 40.

In a preferred form of the present invention, the twist connector 31 allows for releasable connection of the first elongate section 30 and the second elongate section 40 to the handle member 20 in such a manner so as to allow for the transmission of light through the optical cable 27 and into the second elongate section 40, and so as to provide for the secure attachment between the handle member 20 and the first elongate section 30.

As shown in the drawings, the twist connector 31 preferably includes a key and keyway configuration that allows for the secure and quick connection of the first elongate section 30 to the handle member 20. Additionally, a preferred form of this connection 31 includes the increase in resistance turning of these members, and the secure positioning of the shaft shaped portion relative to the end of the optical cable 27 or short cable 56.

The first elongate section 30 and the second elongate section 40 may be quickly removed from the twist connector 31 on the handle member 20 by depressing the connector knob 33, and then rotating the first elongate section and second elongate section at least one-fourth (i.e., 90°) of a complete (i.e., 360°) turn relative to the handle member 20 to release the keys from the keyway.

Thus, use of the twist connector 31 and the connector knob 33 allow medical personnel to quickly and conveniently attach different first elongate sections 30 and/or different second elongate sections 40 to the handle member 20 as desired.

Although a preferred form of the connector 31 between the handle member 20 and the first elongate section 30 is described herein as a twist connector, it is understood that a variety of connections (including, but not limited to bayonet, snap or threaded connections) may be used instead, provided that the optical cable 27 and shaft shaped member of the second elongate section 40 are securely and operatively connected thereby.

Referring now to the first elongate section 30 of the retractor 10, this section includes a first elongate proximal end portion 34, first elongate distal end portion 32, first elongate outer surface 36, first elongate inner surface 38, and shaft portion 35. Certain portions of the first elongate section 30 resemble those of the first elongate section of the retractor depicted and disclosed in U.S. Pat. No. 6,322,499, but certain other aspects are preferably dissimilar thereto in order to optimize the performance of the retractor in the context of a vessel harvesting procedure, wherein the vessel (e.g., the radial artery, the basilic vein) is located in a patient's arm.

For example, the area distal to the first elongate distal end portion 32 of the first elongate section 30 of a retractor of the present invention is generally similar to the comparable area of the retractor depicted and disclosed in U.S. Pat. No. 6,322,499. For example, as the first elongate section 30 extends distally beyond the first elongate distal end portion 32, the first elongate section 30 assumes a generally circular shape to form/define a preferably hollow curved shaft portion 35.

This shaft portion 35 preferably includes a circular bend to form a generally perpendicular or acute angle with respect to the elongate connector and handle member 20. As shown, the shaft portion 35 is also preferably a cylindrical member that includes a side slot 37 that extends lengthwise therealong.

The side slot 37 is formed to receive a portion of the second elongate section 40 laterally inserted therethrough for the connection of the light source to the second elongate section via the twist connector 31.

Additionally, the outer curvature of the shaft portion 35 functions to shield medical personnel from light emitted from the distal portion of the second elongate section 40, so that the light does not reflect into the eyes of medical personnel during the vessel harvesting procedure.

But unlike the embodiments of the first elongate section of the retractor that are depicted and described in U.S. Pat. No. 6,322,499, in a preferred embodiment of the present invention, neither the first elongate outer surface 36 nor the first elongate inner surface 38 of the first elongate section 30 of the retractor 10 extends linearly from the proximal end portion 34 of the first elongate section to a location near the distal end portion 32 of the first elongate section.

Figure 6A:
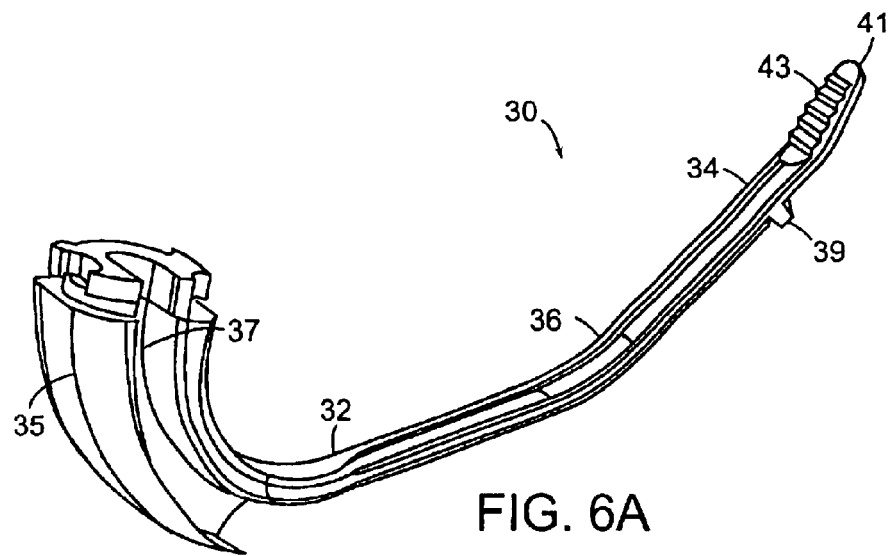
FIGS. 6A–6C are perspective views (FIGS. 6A and 6C) and a front view (FIG. 6B) of a bent first elongate section of an illuminated retractor according to the present invention.
Figure 6B:
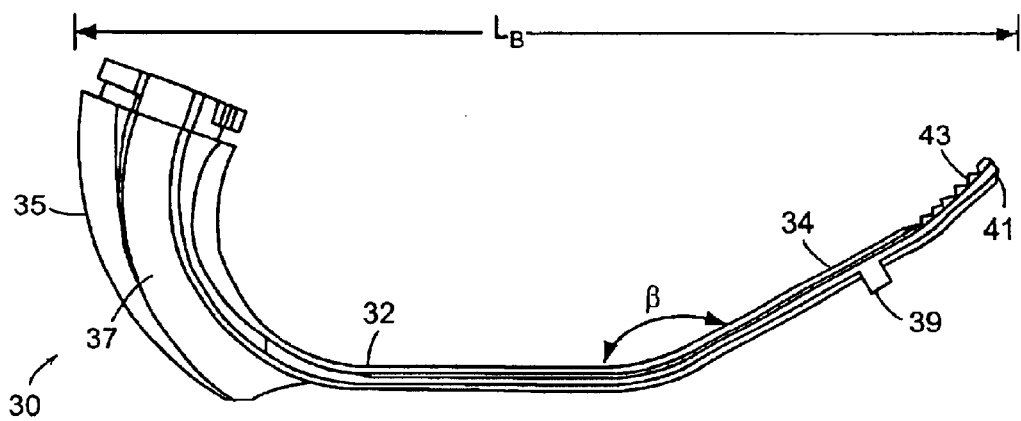
Figure 6C:
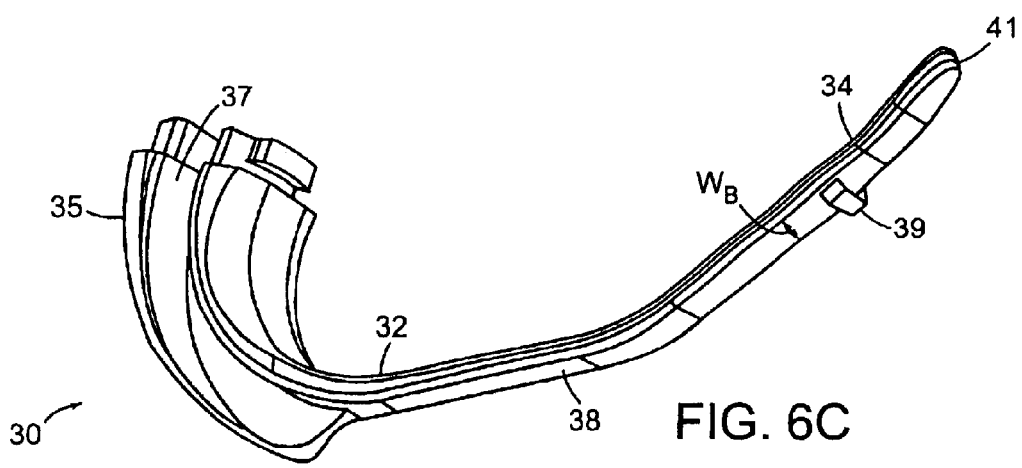

Instead, both these surfaces 36, 38, as well as the area between the first elongate distal end portion 32 and first elongate proximal end portion 34 of the first elongate section 30 of the retractor 10 are at least partially non-linear. By way of non-limiting example, these surfaces 36, 38 and this area can be curved (see FIGS. 1–4, 5A–5C) or bent (see FIGS. 6A–6C) such that the first elongate section 30 has a curved or bent shape/contour.

Although the retractor 10 depicted in FIGS. 1–4 has a curved first elongate surface 10, it is understood that the first elongate surface can, instead, be bent.

In an embodiment in which the retractor 10 includes a curved first elongate section 30, the radius of curvature is generally in the range of about 1.0 inch to 5.0 inches, preferably about 3.0 inches to 5.0 inches, most preferably about 3.5 inches. Although the curvature generally commences at or near the approximate midpoint between the first elongate distal end portion 32 and the first elongate proximal end portion 34 of the first elongate section 30, it is understood that the curvature can commence at any point between these loci 32, 34.

In an embodiment in which the retractor 10 includes a bent first elongate section 30, the vertex of the bending angle, β (see FIG. 6B), generally commences at or near the approximate midpoint between the first elongate distal end portion 32 and first elongate proximal end portion 34 of the first elongate section 30. It is understood, however, that the vertex of the bending angle, β, may be located at any point between these loci 32, 34.

The bending angle, β, may have a range of values, generally between about 80° and about 175°. The bending angle, β, preferably is about 140° to about 160°, most preferably about 150°.

The first elongate section 30 of the retractor 10 of the present invention may have a range of acceptable lengths and widths, wherein such dimensions are selected to allow the first elongate section to enter the narrow (as compared to other vessel sites, e.g., the leg) subcutaneous space within a patient's arm, and to lift and support the skin bridges formed within the patient's arm in furtherance of a radial artery (or, alternatively, a basilic vein) harvesting procedure.

In an exemplary embodiment of the present invention, the first elongate section 30 of the retractor 10 has a length in the range of about 3.0 inches to 8.0 inches, preferably about 4.5 inches to 8.0 inches, most preferably about 4.6 inches to 6.2 inches, and a width in the range of about 0.2 inch to 1.5 inch, preferably about 0.2 inch to 1.3 inch, most preferably about 0.2 inch to 1.2 inch.

While the length, $L_C$ (see FIG. 5B), of a curved first elongate section 30 may be substantially identical to the length, $L_B$ (see FIG. 6B), of a bent first elongate section 30, it is preferable that the length of the former is greater than the length of the latter. In an exemplary embodiment of the present invention, the length, $L_C$, of a curved first elongate section 30 is generally about 0.9 inch greater than the length, $L_B$, of a bent first elongate section 30. Exemplary, and currently preferred, lengths, $L_C$ and $L_B$, of the curved and bent first elongate sections 30 are, respectively, about 5.5 inches and about 4.6 inches.

Similarly, while the width, $W_C$ (see FIGS. 4 and 5C), of a curved first elongate section 30 may be substantially identical to the width, $W_B$ (see FIG. 6C), of a bent first elongate section 30, it is preferable that the width of the former be greater than the width of the latter. In an exemplary embodiment of the present invention, the width, $W_C$, of a curved first elongate section 30 is generally in the range of about 0.3 inch to 0.6 inch greater than the width, $W_B$, of a bent first elongate section 30.

Exemplary, and currently preferred, widths, $W_C$ for the curved bent first elongate section 30 are 0.5 inch and 0.8 inch, while an exemplary, and currently preferred, width, $W_B$, of the bent first elongate section 30 is about 0.2 inch.

In an embodiment in which the first elongate section 30 is substantially straight (i.e., not curved or bent), the section 30 preferably has a length, L, of about 6.2 inches, and a width, W, in the range of about 1.2 inch to 1.3 inch. As noted above, it is believed that such an embodiment is less ideally suited (as compared to an embodiment in which the first elongate section 30 is either curved or bent) for harvesting vessels (e.g., the radial artery or basilic vein) located within a patient's arm.

Although the first elongate section 30 of a retractor 10 in accordance with the present invention may include a shroud member as described and depicted in U.S. Pat. No. 6,322,499, it is preferable that it instead include an insertion area 39 (see FIGS. 1, 2, 4, 5A–5C. 6A–6C, 7A–7C) in order to receive and retain the proximal end portion 44 of the second elongate section 40, and to ensure that these sections 30, 40 remain adjacent to each other during the harvesting procedure.

In a preferred aspect of the invention, the insertion area 39 is a substantially U-shaped flap or loop (see, in particular, FIG. 4) into which the proximal end portion 44 of the second elongate section 40 is laterally insertable. Although the insertion area should protrude from the first elongate section 30 enough to allow for insertion of the second elongate section 40 therein, it should provide a tight, low profile extension that does not deter dissection of the tissue, and that ensures that the inserted second elongate section will not become dislodged therefrom during the harvesting procedure.

The insertion area 39 is generally, but not necessarily, formed of the same material as the remainder of the first elongate section 30, which is preferably made of a material that has sufficient strength to assuredly support the skin bridge during use, and that resists degradation, even after repeated sterilization. Exemplary such materials include, but are not limited to, rigid metals or alloys.

The retractor 10 of the present invention also preferably includes a bent dissecting tip 41, which extends from proximal end portion 35 of the first elongate section 30. This tip 41 allows medical personnel to use the retractor 10 as a dissecting device while the retractor is being maneuvered into, around and/or through the connective tissue and muscle surrounding the radial artery. The tip 41 may include (and preferably does include) serrations 43 thereupon to assist in the dissection of the tissue, and to impede unintended movement of the retractor from its desired position during the harvesting procedure.

The second elongate section 40 of the retractor 10 generally is similar to the corresponding section of the retractor described in U.S. Pat. No. 6,322,499 with respect to the materials from which it is made, its function, and the placement of its components.

Figure 4:
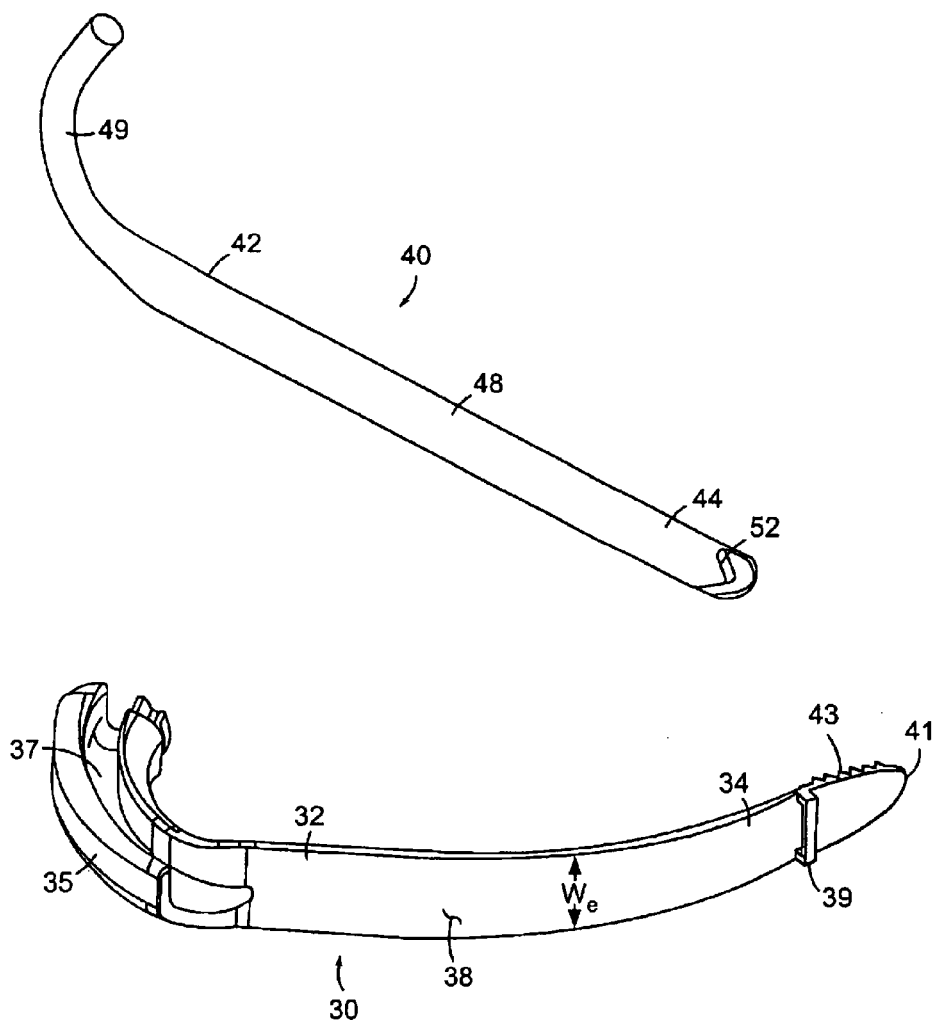
FIG. 4 is a perspective view of a curved first elongate section and a substantially linear second elongate section of an illuminated retractor according to the present invention, and showing the relationship between the first and second elongate sections.
Figure 5A:
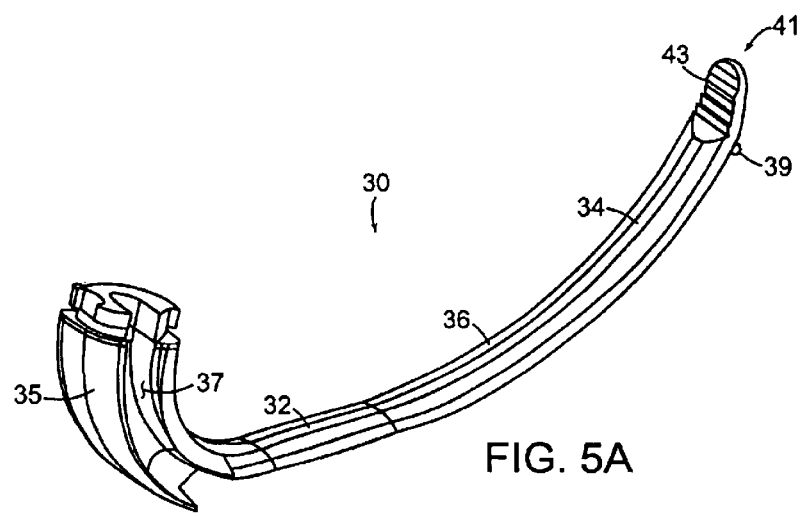
FIGS. 5A–5C are perspective views (FIGS. 5A and 5C) and a front view (FIG. 5B) of a curved first elongate section of an illuminated retractor according to the present invention.
Figure 5B:
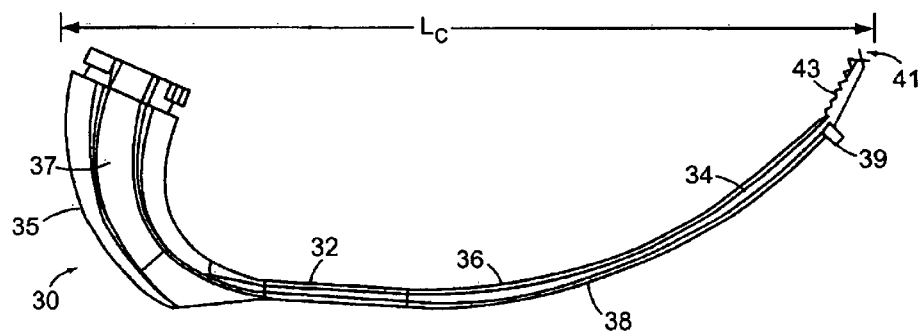
Figure 5C:
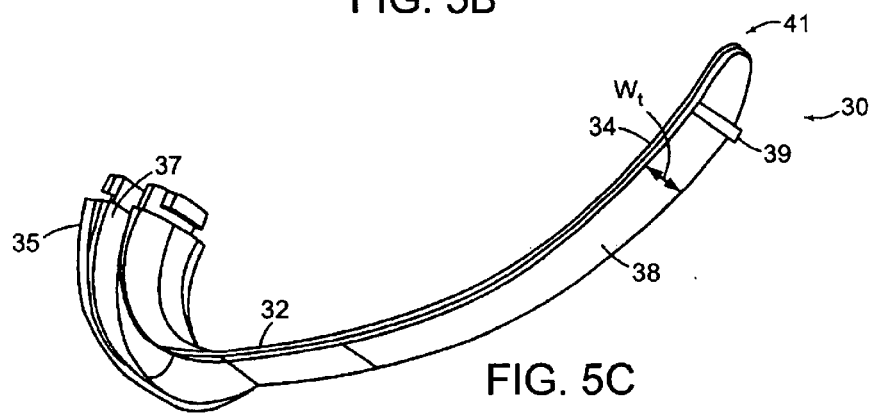

In fact, as shown in FIG. 4, in an embodiment in which the first elongate section 30 of the retractor is curved, the second elongate section 40 generally is substantially identical in shape to the substantially linear second elongate section that is described in U.S. Pat. No. 6,322,499. Upon being inserted into the first elongate section 30, the substantially linear second elongate section 40 assumes a curved condition, wherein it adopts a substantially identical radius of curvature to the curved first elongate section until it is removed from the curved first elongate section, wherein it reverts to its substantially straight shape.

This curved condition of the second elongate section 40 is depicted in FIGS. 1, 2, 7A and 7B.

To enable the substantially straight/linear second elongate section 40 to safely (i.e., without risk of breakage even after repeated insertions) adopt this reversible curved condition upon being inserted into the curved first elongate section 30, the second elongate section is preferably made of a material that is highly resistant to breakage, but that retains the ability to flex or deform under pressure and then return, undamaged, to its original, unstressed configuration.

The material also is preferably transparent to accentuate the illuminate of the second elongate section 40.

By way of non-limiting example, the second elongate section 40 may be made of a semi-rigid, transparent material, such as an acryl resin.

It is understood that the second elongate section 40 may, instead, be formed of a different material, and/or may be either curved in shape or differently contoured while still being insertable into a curved first elongate section 30. The primary purpose for utilizing a substantially straight second elongate section 40 in connection with the curved first elongate section 30 is for economy of parts.

In an embodiment (see FIGS. 6A–6C) in which the first elongate section 30 of the retractor is bent, however, the second elongate section 40 generally should also be bent. Preferably, the second elongate section 40 has a bent shape/contour that is substantially identical to the bent first elongate section 30 prior to being inserted therein, such that the shape of the second elongate section 40 preferably does not substantially change upon being inserted into the first elongate section 30.

Whether or not the first elongate member 30 is curved or bent in shape/contour, the second elongate section 40 will have a second elongate proximal end portion 44, a second elongate distal end portion 42, a second elongate outer surface 46, a second elongate inner surface 48 and a shaft shaped portion 49.

As the second elongate section 40 extends distally beyond the second elongate distal end portion 42, the second elongate section tapers into a shaft shaped member 49 which then curves to match the curvature and inner dimensions of the shaft portion 35 of the first elongate section 30, and which is receivable through the side slot 37. The tapered aspect of the shaft shaped member 49 of the second elongate section 40 allows the transition between the shaft shaped member and the distal end portion 42 of the second elongate section 40 to be surrounded by the distal end portion 32 and shaft portion 35 of the first elongate section 30, in order to minimize the glare from the shaft shaped member and the distal portion of the second elongate section, and also to protect the shaft shaped member as it curves and extends to the twist connector 31.

Furthermore, the shaft shaped member 49 of the second elongate section 40 is preferably spaced apart from the inner surface of the shaft portion 35 of the first elongate section 30, in order to reduce the potential for the buildup of heat from the light energy passing through the second elongate section.

The second elongate outer surface 46 and the second elongate inner surface 48 correspondingly are eliminated as the second elongate section 40 tapers into the shaft shaped member 49.

The second elongate section 40 may be connected to the first elongate section 30 by inserting the second elongate proximal end portion 44 into the insertion area 39 of the first elongate section. Either while this occurs, or, preferably, thereafter, the second elongate member distal end portion 42 and shaft shaped member 49 of the second elongate section 40 are inserted, respectively, into the shaft portion 35 and side slot 37 of the first elongate section 30. This series of insertions are effective to securely retain the second elongate section 40 adjacent to the first elongate section 30, and to engage the optical cable 27 with the second elongate section through the twist connector 31.

The proximal end portion 44 of the second elongate section 40 may include a chamfered surface 52 (see FIG. 4), which, if included, is preferably at an angle of between about 30° and 60°, and, more preferably, at an angle of about 45°. The surface 52 functions similar to a headlight, whereby it projects light from the forward end of the second elongate section 40 and beyond the end of the retractor 10. Therefore, light is preferably passed outwardly from the second elongate section 40 and forwardly from the chamfered surface 52 to illuminate the subcutaneous space defined by the retractor 10.

Alternately, the second elongate section 40 may be connected to the first elongate section 30 in any manner known in the art that is within the level of ordinary skill of one in the surgical field. For example, although less desirable than the manner of attachment described above, the second elongate outer surface 46 may be chemically bonded to the first elongate inner surface 38 through the use of an adhesive, or by other chemical bonding means known to one skilled in the art.

Such chemical bonding may permanently affix the first and second elongate sections 30, 40 or may preferably allow these elongate sections 30, 40 to be releasably connected for ease of sterilization of the sections. Alternately, if the second elongate section 40 is a light fiber element, the light fiber element may be threaded through various retention members located along the lengthwise dimension of the first elongate section 30.

The second elongate proximal end portion 44 of the second elongate section 40 has a rounded shape or, alternatively, a smoothly radiused pointed shape. The shape of the second elongate proximal end portion 44 is sized to be securely received in the insertion area 39 of the first elongate section such that flexing of any portion of the first or second elongate sections 30, 40 will not separate/free the second elongate section from the insertion area 39.

The curved or bent shape/contour of the first elongate section 30 has several notable benefits, some of which are of particular benefit in connection with a vessel harvesting procedure, wherein the vessel (e.g., radial artery, basilic vein) is located in a patient's arm. For example, in an embodiment in which the first elongate section 30 is curved, the first elongate outer surface 36 is convex. The convex cross-sectional shape of the first elongate outer surface 36 of the first elongate section 30 aids in the prevention of unnecessary trauma to the retracted tissue because the first elongate outer surface 36, which is in contact with the subcutaneous tissue when the pulling force is applied to the retractor 10, presents no sharp edges that could cause tearing of the tissue. This shape also aids in distributing the force applied to the retracted tissue by the first elongate section 30.

Another significant benefit is realized if the first elongate section 30 is either curved or bent as described above. This curved or bent shape allows the retractor 10 of the present invention to be used in a manner that minimizes the portion of the retractor that is either within the subcutaneous space and/or that impedes access to the space, especially in comparison to the retractor described and depicted in U.S. Pat. No. 6,322,499.

Because of the bent or curved shape of the first elongate section 30 of the retractor 10, the first elongate distal end portion 32 and the first elongate proximal portion 34 are not parallel to each other. Thus, it is possible to insert the area of the first elongate section 30 that is proximal to the first elongate proximal end portion 32 into the subcutaneous space, while the remainder of the first elongate section is located outside of that subcutaneous space.

Moreover, the portion of the first elongate section 30 that is outside of the subcutaneous space, by virtue of the non-linear aspect of the first elongate section, will be positioned more remotely from this space as compared to a linear first elongate section, such as the retractor depicted and described in U.S. Pat. No. 6,322,499.

Based on the linear geometry of the retractor in U.S. Pat. No. 6,322,499, the portion of the first elongate section of that retractor located outside of the subcutaneous space while the retractor is being used to retract tissue will protrude from the subcutaneous space in a direction substantially parallel to the portion within the space, thus limiting access into and near the subcutaneous space.

In contrast, the portion of a non-linear (i.e., curved or bent) first elongate section 30 that protrudes from the subcutaneous space is not parallel to the portion contained therein. Rather, the protruding portion of the curved/bent first elongate section 30 will be located above the axis of the portion of that is within the subcutaneous space. This allows the protruding portion to be more remotely located from the subcutaneous space, and, in turn, allows for improved access into and near the subcutaneous space as compared to a linear first elongate section.

Although not shown in the drawings, it is understood that in accordance with the present invention, the elongate outer surface 36 of the first elongate section 30 may be concave, such as wherein the first elongate section is oppositely curved than as shown in the drawings.

As will be obvious to one skilled in the art, however, if a complementary fit of the second elongate outer surface 46 of the second elongate section 40 and the inner surface 38 of a curved first elongate section 30 is desired, the outer surface 46 of the second elongate section 40 may have nearly any geometric cross-section that allows the second elongate outer surface 46 to complementarily fit against the inner surface 38 of the first elongate section 30, as there is no requirement that the first elongate inner surface 38 be concave in cross-section.

There is also no constraint requiring that the outer surface 46 of the second elongate section 40 be complementarily shaped to the inner surface 38 of a curved first elongate section 30. Rather, the only constraint on the shape of the geometric cross-section of the second elongate section 40 is that the chosen geometric cross-section should allow the second elongate section 40 to be protected, by means known in the art, by the first elongate section 30 such that the first and second elongate sections 30, 40 are preferably operatively interconnected and complementary to each other.

In an embodiment wherein the first elongate section 30 is bent, however, it is preferably that the second elongate section 40 also be bent, preferably to substantially compliment the particular bent shape of the first elongate section. Also, it is preferred that the second elongate section be bent prior to being inserted within the first elongate section, such that the shape of the second elongate section 40 preferably does not change upon being inserted into the first elongate section 30.

The primary reason for this is that although the second elongate section (by virtue of being made of material that is highly resistant to breakage, but that retains the ability to flex or deform under pressure and then return undamaged to the original, unstressed configuration) can bend into a curved condition, wherein it reversibly adapts to the shape of a curved first elongate section without fear of damage to second elongate section, it is believed that adaptation of a non-bent second elongate section into a bent condition wherein it substantially assumes the shape of a bent first elongate section could compromise (either immediately or, more likely, over time) the structural integrity of the second elongate section, due to the increased stress/pressure placed upon the second elongate section at the vertex of the bending angle, $\beta$.

In order to enhance the reflective qualities of the retractor 10, the first elongate inner surface 38 of the first elongate section 30 preferably has a mirrored or reflective surface. Also, the second elongate inner surface 48 of the second elongate section 40 preferably has a machined micro lens surface to refract the light in the desired direction(s). The mirrored surface of the first elongate inner surface 38, and the surface of the second elongate inner surface 48 act to minimize the loss of the light intensity that is provided to the surgical field by the illuminated retractor 10.

Alternately, the second elongate inner surface 48 may include a reflective coating or graded dot surface thereon to reflect the light generated through the second elongate section 40 outwardly through the second elongate outer surface 46. Additionally, the second elongate section 40 may be formed so as to specifically direct the light forwardly or towards the proximal end of the retractor to, in turn, direct the illumination forwardly beyond the second elongate proximal end portion 44, thereby assisting medical personnel by illuminating the area of interest.

Because the second elongate section 40 of the present invention is readily removable once inserted into the first elongate section 30, it is anticipated that a variety of second elongate sections may be used, including second elongate sections that are formed to direct the illumination forwardly and/or to one or both sides of the retractor 10 as desired and/or as dictated by the nature of the harvesting procedure.

As shown, the illumination from the retractor is preferably at an angle of about 45° forwardly of the retractor 10, although this forward orientation of the light may be oriented to be between 30° and 90° with respect to the lengthwise dimension of the retractor. Similarly, the second elongate section 40 may be formed to direct light sideways from the retractor 10 at an angle of between about 15° and 90°, and, more preferably, about 45° with respect to the retractor 10.

In an exemplary embodiment of the present invention, light energy passes from the light source, through the optical cable 27, and enters the second elongate section 30 of the retractor 10 at the end portion of the shaft shaped member 49 adjacent to the twist connector 31.

Figure 7A:
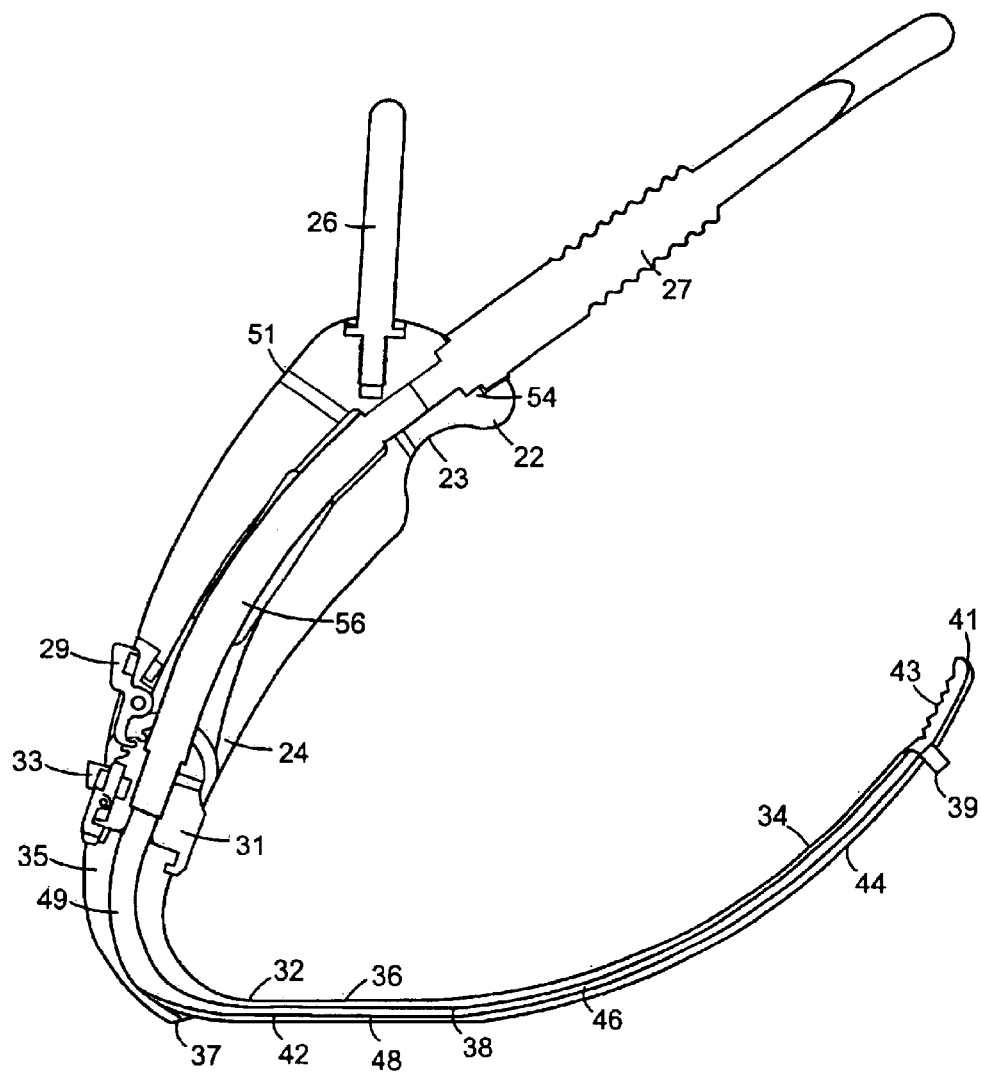
FIGS. 7A and 7B are enlarged side views of an alternate preferred form of an illuminated retractor according to the present invention with a connector at the upper end of the handle member for connecting a standard optical cable to a short optical cable in the handle member.
Figure 7B:
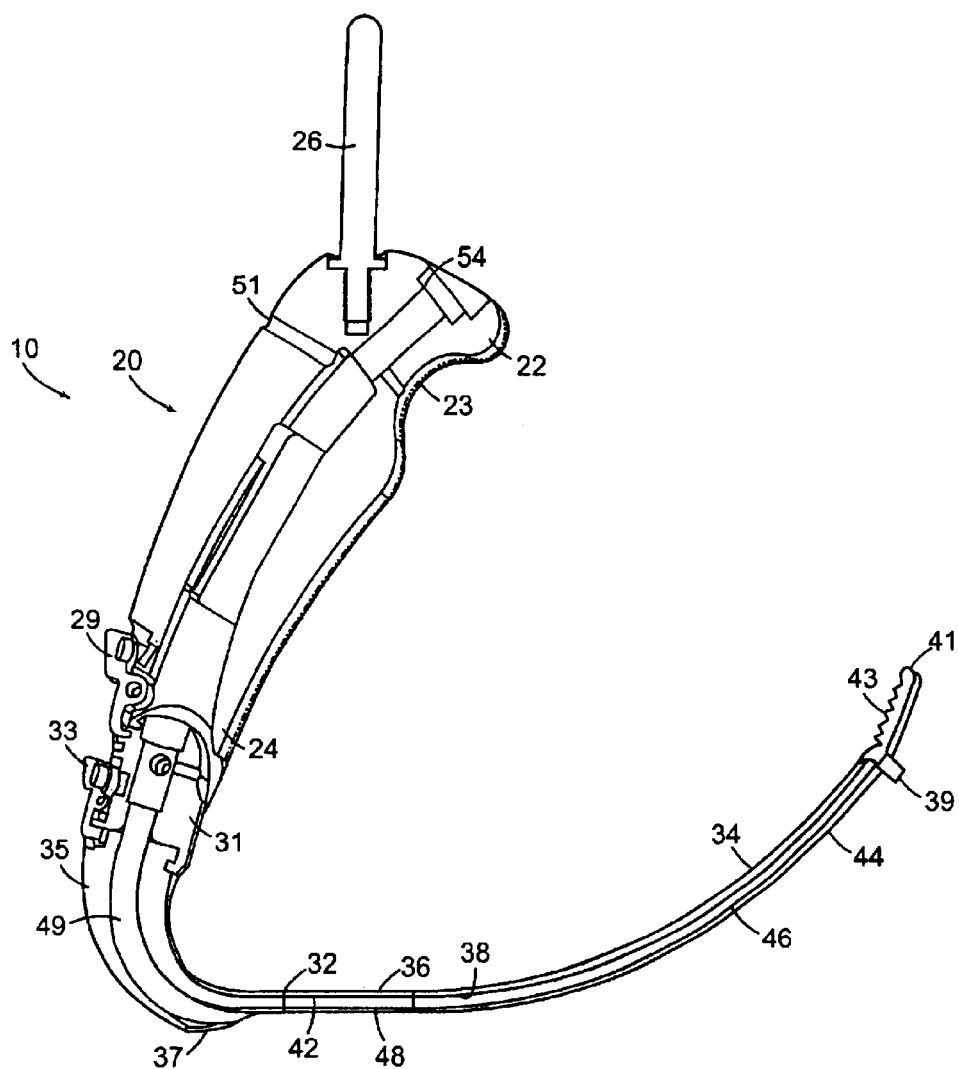

In an alternate, yet preferred embodiment shown in FIGS. 7A and 7B, the light energy passes from the light source, through the optical cable 27, to the second connector 54 and into the short cable 56. From the short cable 56, the light energy passes to the twist connector 31 and into the shaft shaped member 49 of the second elongate section 30.

The shaft shaped member 49 of the second elongate section 40 directs the illumination to the second elongate distal end portion 42 of the second elongate section 40, and allows light energy to enter the second elongate section 40. The light energy fills the second elongate section 40 and is radiated therefrom, particularly from the inner surface 48 of the second elongate section 40 between the distal end portion 42 and proximal end portion 44 of the second elongate section, and preferably from the chamfered surface 52 (if included) on the proximal end portion 44 of the second elongate section.

The light is then directed into the subcutaneous space defined/exposed by the retractor 10. Since substantially the entire length of the second elongate section 40 is illuminated, a large, well-illuminated surgical field extends the substantial length of the second elongate section 40 of the retractor 10. This allows medical personnel to visualize tissue, muscle, and, ultimately, the vessel (e.g., the radial artery) to be harvested. Such visualization is achieved in a minimally invasive manner, and without the need for viewing the surgical field through endoscopic visual devices.

The twist connector 31 couples the optical cable 27 to the shaft shaped member 49 of the second elongate section 40. The twist connector 31 is adapted to receive and releasably retain the shaft portion 35 of the first elongate section and the shaft shaped member 49 of the second elongate section therein to couple the shaft shaped member 49 to the optical cable 27, and to connect the first elongate section to the handle member 20. In this manner, light can be provided from the light source via the optical cable 27 to the shaft shaped member 49 of the second elongate section 40 so that the second elongate section 40 is illuminated.

Referring further to the drawings, the tip 41 of the first elongate section 30 preferably has a rounded shape or a smoothly-radiused, pointed shape that allows the retractor 10 to be pushed into the small, transverse incision(s) made by medical personnel, and to be maneuvered through tissue within the subcutaneous space.

The tip 41 preferably has an outer surface that includes a plurality of dissecting serrations 43 thereon. Each of these serrations 43 is preferably oriented at a substantial right angle to the lengthwise dimension of the upper proximal portion of the tip 41.

It is contemplated that the serrations 43 may be placed at an angle, other than the right angle described above, relative to the upper proximal portion of the tip 41. It is also contemplated that the serrations 43 might be placed at a series of angles to form a graphic series of serrations 43 (e.g., a plurality of arrow, or v-shaped, serrations 43 with the point of the arrow oriented toward the proximal end portion 34 of the first elongate section 40) to increase the tissue gripping ability of his portion of the retractor 10.

One purpose of tip 41 of the retractor 10 is to assist medical personnel translate some of the applied force to the retractor 10 into a dissecting force by letting the tip 41, with the dissecting serrations 43, perform some of the required dissecting work. By using the retractor 10 to accomplish some of the dissecting required by the vessel harvesting procedure, medical personnel can, while still performing the procedure in a less invasive manner, more rapidly complete the surgical procedure, thus resulting in reduced surgical time, and a reduced possibility of trauma to the patient from the surgery.

The present invention has been described in reference to use in harvesting blood vessels. It would be obvious to one skilled in the art, however, that the present invention could also be used in other minimally invasive surgical procedures in which the illumination of the minimally invasive surgical field is desired. Further, although the present invention has been described with reference to specific details of preferred embodiments thereof, it is not intended that such detail should be regarded as limiting the scope of the invention, except as and to the extent that they are included in the accompanying claims. Moreover, all documents mentioned herein are incorporated by reference herein in their entirety.

What is claimed is:

1. An illuminated surgical retractor comprising:
    a handle member having a first handle member end portion and a second handle member end portion;
    a first elongate section having a first elongate proximal end portion, a first elongate distal end portion, and a first elongate inner surface extending from the first elongate proximal end portion to near the first elongate distal end portion and having a substantially non-linear shape in the longitudinal direction, the second handle member end portion of said handle member pivotally connected to the first elongate distal end portion of said first elongate section such that said handle member forms an adjustable acute angle with said first elongate section;
    a second elongate section having a second elongate proximal end portion, a second elongate distal end portion, and a second elongate outer surface extending from the second elongate proximal end portion to near the second elongate distal end portion, and a second elongate inner surface extending from the second elongate proximal end portion to near the second elongate distal end portion, said second elongate section connected to said first elongate section such that said first and second elongate sections are substantially parallel; and
    said second handle member end portion having a pivotal connector associated therewith and said pivotal connector pivotally couples the first elongate section and the handle member and said second handle member end portion is adapted to optically couple the second elongate section to a source of illumination so that said second elongate section is substantially illuminated.

2. The illuminated surgical retractor of claim 1, wherein the shape of the first elongate inner surface is selected from the group consisting of curved and bent.

3. The illuminated surgical retractor of claim 2, wherein the shape of the first elongate inner surface is bent, and wherein the second elongate outer surface has a bent shape that substantially corresponds to the bent shape of the first elongate inner surface.

4. The illuminated surgical retractor of claim 3, wherein the first elongate inner surface is bent at an angle in the range of about 80° to 175°.

5. The illuminated surgical retractor of claim 4, wherein the first elongate inner surface is bent at an angle in the range of about 140° to 160°.

6. The illuminated surgical retractor of claim 2, wherein the shape of the first elongate inner surface is curved, and has a radius of curvature in the range of about 1.0 inch to 5.0 inches.

7. The illuminated surgical retractor of claim 6, wherein the second elongate outer surface has a shape that differs from the curved shape of the first elongate section prior to connection thereof to the first elongate section, and that substantially conforms to the shape first elongate section following connection thereof to the first elongate section.

8. The illuminated surgical retractor of claim 7, wherein the conformation of the shape of the second elongate section to the first elongate section is reversible upon disconnecting the first elongate section and the second elongate section.

9. The illuminated surgical retractor of claim 1, wherein the proximal end portion of the second elongate section culminates in a chamfered surface at an angle in the range of about 30° to 60°.

10. An illuminated surgical retractor comprising:
   a handle member having a first handle member end portion and a second handle member end portion;
   a first elongate section having a lengthwise dimension and a first elongate proximal end portion, a first elongate distal end portion, and a first elongate inner surface extending from the first elongate proximal end portion to near the first elongate distal end portion and having a substantially non-linear shape there between, the second handle member end portion of said handle member operatively connected to the first elongate distal end portion of said first elongate section such that said handle member forms an acute angle with said first elongate section;
   a second elongate section having a lengthwise dimension and a second elongate proximal end portion, a second elongate distal end portion and a second elongate outer surface extending from the second elongate proximal end portion to near the second elongate distal end portion, and a second elongate inner surface extending from the second elongate proximal end portion to near the second elongate distal end portion, said second elongate section being generally aligned with the lengthwise dimension of the first elongate section, said second elongate section defining an illumination output portion; and
   said second handle member end portion having a pivotal connector associated therewith and said pivotal connector pivotally couples the first elongate section and the handle member and said second handle member end portion is adapted to optically couple the second elongate section to a source of illumination so that said second elongate section is illuminated.

11. The illuminated surgical retractor of claim 10, wherein the shape of the first elongate inner surface is selected from the group consisting of curved and bent.

12. The illuminated surgical retractor of claim 11, wherein the shape of the first elongate inner surface is bent, and wherein the second elongate outer surface has a bent shape.

13. The illuminated surgical retractor of claim 12, wherein the first elongate inner surface is bent at an angle in the range of about 80° to 175°.

14. The illuminated surgical retractor of claim 11, wherein the shape of the first elongate inner surface is curved, and has a radius of curvature in the range of about 1.0 inch to 5.0 inches.

15. The illuminated surgical retractor of claim 14, wherein the second elongate outer surface has a shape that differs from the curved shape of the first elongate section prior to connection thereof to the first elongate section, and that substantially conforms to the shape first elongate section following connection thereof to the first elongate section.

16. The illuminated surgical retractor of claim 15, wherein the conformation of the shape of the second elongate section to the first elongate section is reversible upon disconnecting the first elongate section and the second elongate section.

17. The illuminated surgical retractor of claim 10, wherein at least a portion of said second elongate section is surrounded by at least a portion of said elongate section includes an insertion area shaped to receive at least a portion of said second elongate section therein.

18. The illuminated surgical retractor of claim 10, wherein the first elongate section includes an insertion area shaped to receive at least a portion of said second elongate section therein.

19. The illuminated surgical retractor of claim 18, wherein the insertion area of the first elongate section is a substantially U-shaped flap.

20. The illuminated surgical retractor of claim 10, wherein the proximal end portion of the second elongate section culminates in a chamfered surface at an angle in the range of about 30° to 60°.

21. An illuminated surgical retractor for use in a patient comprising:
   a handle member having a first handle member end portion and a second handle member end portion;
   a first elongate section having a first elongate proximal end portion, a first elongate distal end portion, and a first elongate inner surface extending from the first elongate proximal end portion to near the first elongate distal end portion and having a substantially non-linear shape in the longitudinal direction, the second handle member end portion of said handle member connected to said first elongate section such that said handle member forms an acute angle with said first elongate section;
   a second elongate section having a second elongate proximal end portion, a second elongate distal end portion and a second elongate outer surface extending from the second elongate proximal end portion to near the second elongate distal end portion, and a second elongate inner surface extending from the second elongate proximal end portion to near the second elongate distal end portion, said second elongate section connected to said first elongate section such that said first and second elongate sections are substantially aligned, the second elongate distal end portion of said second elongate section defining an illumination output member; and
   an insertion area on the proximal end portion of the first elongate section for the receipt of at least a portion of the second elongate section therein.

22. The illuminated surgical retractor of claim 21, wherein the insertion area is a substantially U-shaped flap.

23. The illuminated surgical retractor of claim 21, wherein the shape of the first elongate inner surface is selected from the group consisting of curved and bent.

24. The illuminated surgical retractor of claim 23, wherein the shape of the first elongate inner surface is bent, and wherein the second elongate outer surface has a bent shape that substantially corresponds to the bent shape of the first elongate inner surface.

25. The illuminated surgical retractor of claim 24, wherein the first elongate inner surface is bent at an angle in the range of about 80° to 175°.

26. The illuminated surgical retractor of claim 23, wherein the shape of the first elongate inner surface is curved, and has a radius of curvature in the range of about 1.0 inch to 5.0 inches.

27. The illuminated surgical retractor of claim 26, wherein the second elongate outer surface has a shape that differs from the curved shape of the first elongate section prior to connection thereof to the first elongate section, and that substantially conforms to the shape first elongate section following connection thereof to the first elongate section.

28. The illuminated surgical retractor of claim 27, wherein the conformation of the shape of the second elongate section to the first elongate section is reversible upon disconnecting the first elongate section and the second elongate section.

29. The illuminated surgical retractor of claim 21, wherein said handle member is operatively connected to said first elongate section by a pivotal connector.

30. The illuminated surgical retractor of claim 29, wherein said pivotal connector enables said second elongate section to be interchangeable with respect to the first elongate section.

31. The illuminated surgical retractor of claim 21, wherein at least a portion of said first elongate section substantially surrounds at least a portion of said second elongate section, and said at least a portion of said second elongate section is removable therethrough.

32. The illuminated surgical retractor of claim 21, wherein said second elongate section is laterally insertable into engagement with said first elongate section.

33. The illuminated surgical retractor of claim 21, wherein said first elongate section is rotatable with respect to said handle member for removal therefrom.

34. The illuminated surgical retractor of claim 21, wherein the proximal end portion of the second elongate section culminates in a chamfered surface at an angle in the range of about 30° to 60°.

35. An illuminated surgical retractor comprising:
a handle member having a first handle member end portion and a second handle member end portion and at least a portion thereof that is illuminated in use;
a first elongate section having a first elongate proximal end portion, a first elongate distal end portion, and a first elongate inner surface extending from the first elongate proximal end portion to near the first elongate distal end portion and having a substantially curved shape in the longitudinal direction, the second handle member end portion of said handle member connected to the first elongate distal end portion of said first elongate section such that said handle member is pivotal with respect thereto and forms an acute angle with said first elongate section;
a second elongate section having a second elongate proximal end portion, a second elongate distal end portion, and a second elongate outer surface extending from the second elongate proximal end portion to near the second elongate distal end portion, and a second elongate inner surface extending from the second elongate proximal end portion to near the second elongate distal end portion, the second elongate distal end portion of said second elongate section defining an illumination output member.

36. The illuminated surgical retractor of claim 35, wherein the curved first elongate inner surface has a radius of curvature in the range of about 1.0 inch to 5.0 inches.

37. The illuminated surgical retractor of claim 36, wherein the second elongate outer surface has a shape that differs from the curved shape of the first elongate section prior to connection thereof to the first elongate section, and that substantially conforms to the shape first elongate section following connection thereof to the first elongate section.

38. The illuminated surgical retractor of claim 37, wherein the conformation of the shape of the second elongate section to the first elongate section is reversible upon disconnecting the first elongate section and the second elongate section.

39. The illuminated surgical retractor of claim 35, wherein said second elongate section includes a shaft shaped portion that is substantially enclosed by at least a portion of said first elongate section.

40. The illuminated surgical retractor of claim 35, wherein said first elongate section is pivotal with respect to said handle member.

41. The illuminated surgical retractor of claim 35, wherein the acute angle formed between said handle member and said first elongate section is pivotal from about 30° to 95°.

42. The illuminated surgical retractor of claim 35, wherein the proximal end portion of the second elongate section culminates in a chamfered surface at an angle in the range of about 30° to 60°.

43. An illuminated surgical retractor comprising:
a handle member having a first handle member end portion and a second handle member end portion;
a first elongate section having a first elongate proximal end portion and a first elongate distal end portion, with a first elongate inner surface extending between the first elongate proximal end portion and the first elongate distal end portion, the first elongate inner surface having a substantially bent shape, wherein the first elongate inner surface is bent at an angle in the range of about 80° to 175°, wherein said second handle member end portion of said handle member is connected to said first elongate section;
a second elongate section having a second elongate proximal end portion and a second elongate distal end portion with a second elongate outer surface extending between the second elongate proximal end portion and the second elongate distal end portion, a second elongate inner surface extending between the second elongate proximal end portion and the second elongate distal end portion, the second elongate distal end portion of said second elongate section defining an illumination input end portion;
a connector releasably coupling the illumination input end portion to an optical cable; and
a pivotal connector pivotally coupling the handle member to the first elongate section.

44. An illuminated surgical retractor comprising:
a handle member having a first handle member end portion and a second handle member end portion;
a first elongate section having a first elongate proximal end portion and a first elongate distal end portion, with a first elongate inner surface extending between the first elongate proximal end portion and the first elongate distal end portion, the first elongate inner surface having a substantially bent shape, wherein said second handle member end portion of said handle member is connected to said first elongate section;

a second elongate section having a second elongate proximal end portion and a second elongate distal end portion with a second elongate outer surface extending between the second elongate proximal end portion and the second elongate distal end portion, a second elongate inner surface extending between the second elongate proximal end portion and the second elongate distal end portion, the second elongate distal end portion of said second elongate section defining an illumination input end portion, wherein the proximal end portion of the second elongate section culminates in a chamfered surface at an angle in the range of about 30° to 60°, a connector releasably coupling the illumination input end portion to an optical cable; and a pivotal connector pivotally coupling the handle member to the first elongate section.

45. An illuminated surgical retractor for illuminating the subcutaneous space between a vessel and the subcutaneous tissue of a patient, the retractor comprising:

a handle member having a first handle member end portion and a second handle member end portion with a gripping area there between for gripping by the user and an optical cable extending therethrough;

a first elongate section having:
 a first elongate proximal end portion, and
 a first elongate distal end portion with a first elongate inner surface extending between the first elongate proximal end portion and the first elongate distal end portion, said first elongate inner surface having a substantially bent shape, wherein the angle of bending of the first elongate surface is in the range of about 80° to 175°, the second handle member end portion of said handle member being connected to the first elongate section;

a second elongate section being formed to direct light laterally therefrom, and beyond the first elongate section, the second elongate section having:
 a second elongate proximal end portion that culminates in a chamfered surface at an angle in the range of about 30° to 60°, and a second elongate distal end portion with a second elongate inner surface and a second elongate outer surface each extending between the second elongate proximal end portion and the second elongate distal end portion, the second elongate inner and outer surfaces each having a bent shape that substantially corresponds to the bent shape of the first elongate inner surface, the second elongate section further including an illumination input end portion thereon, wherein at least a portion of said illumination input end portion is substantially surrounded by a portion of said first elongate section;

a connector optically coupling the illumination input end portion to the optical cable;

a pivotal connector for pivotally connecting the handle member and the first elongate section such that the first elongate section is movable at an acute angle relative the handle member; and a substantially U-shaped flap extending from the first elongate section and into which the second elongate section is insertable, wherein at least a portion of said second elongate section, once inserted into the insertion area of the first elongate section, is laterally removable therefrom.

\* \* \* \* \*